US 6,641,569 B1

(12) United States Patent
Coles et al.

(10) Patent No.: US 6,641,569 B1
(45) Date of Patent: *Nov. 4, 2003

(54) DISPOSABLE HUMAN WASTE MANAGEMENT DEVICE WITH IMPROVED ADHESIVE FOR SKIN ATTACHMENT

(75) Inventors: Peter Coles, Kriftel (DE); Fabio Cinelli, Bologna (IT); Italo Corzani, Chieti (IT); Hugh Semple Munro, Chipping Camden (GB); Mohammed Yasin, Birmingham (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/744,889

(22) PCT Filed: Jun. 30, 1999

(86) PCT No.: PCT/GB99/02518

§ 371 (c)(1),
(2), (4) Date: Mar. 22, 2001

(87) PCT Pub. No.: WO00/07637

PCT Pub. Date: Feb. 17, 2000

(30) Foreign Application Priority Data

Jul. 31, 1998 (GB) ............................................. 9816826

(51) Int. Cl.[7] .......................... A61F 13/15; A61F 13/20; A61F 5/44

(52) U.S. Cl. .................. 604/385.19; 604/332; 604/345; 604/355

(58) Field of Search ............................... 604/327, 332, 604/336, 339, 342–345, 352, 355, 364, 368, 385.19, 386

(56) References Cited

U.S. PATENT DOCUMENTS

| 4,445,898 A | * | 5/1984 | Jensen ........................ 604/332 |
| 4,681,574 A | * | 7/1987 | Eastman ..................... 604/344 |
| 4,699,146 A | * | 10/1987 | Sieverding ............. 252/519.21 |
| 5,173,302 A | * | 12/1992 | Holmblad et al. .......... 424/448 |
| 5,234,992 A | * | 8/1993 | Gyory et al. .................. 524/47 |
| 5,338,490 A | * | 8/1994 | Dietz et al. ................. 252/500 |
| 5,670,557 A | * | 9/1997 | Dietz et al. ................. 522/184 |
| 5,927,282 A | * | 7/1999 | Lenker et al. .............. 128/885 |
| 6,160,200 A | * | 12/2000 | Ehrnsperger et al. ....... 604/378 |
| 6,177,482 B1 | * | 1/2001 | Cinelli et al. ........... 428/355 R |
| 6,191,189 B1 | * | 2/2001 | Cinelli et al. ........... 428/355 R |
| 6,211,263 B1 | * | 4/2001 | Cinelli et al. ........... 428/355 R |
| 6,350,256 B1 | * | 2/2002 | Palumbo et al. ............ 604/327 |
| 6,398,768 B1 | * | 6/2002 | Palumbo et al. ............ 604/327 |
| 6,406,464 B1 | * | 6/2002 | Palumbo et al. ............ 604/327 |
| 6,447,798 B1 | * | 9/2002 | Munro et al. ............... 424/443 |
| 2002/0013565 A1 | * | 1/2002 | Cinelli et al. .......... 604/385.03 |
| 2002/0013568 A1 | * | 1/2002 | Cinelli et al. ............. 604/387 |
| 2002/0034492 A1 | * | 3/2002 | Munro et al. ............. 424/78.36 |
| 2002/0035320 A1 | * | 3/2002 | Munro et al. ............... 600/391 |
| 2002/0037270 A1 | * | 3/2002 | Munro et al. ............. 424/78.17 |

FOREIGN PATENT DOCUMENTS

| EP | 0 012 402 A1 | * | 6/1980 | |
| EP | 0 676 457 A1 | * | 10/1995 | |
| GB | 2 284 767 A1 | * | 6/1995 | |
| WO | WO 9717926 A1 | * | 5/1997 | .......... A61F/13/58 |
| WO | WO 00/06214 A1 | * | 2/2000 | |
| WO | WO 00/07636 A1 | * | 2/2000 | |

* cited by examiner

Primary Examiner—Karin Reichie
(74) Attorney, Agent, or Firm—Peter D. Meyer

(57) ABSTRACT

A disposable human waste management device, such as faecal and urine management devices (10), which are provided with adhesives for attachment of the device to the skin. Such adhesives (20) provide secure attachment and are pleasing to the skin upon application, yet cause no discomfort upon removal. The device may also be used in combination with a disposable diaper.

12 Claims, 5 Drawing Sheets

DISPOSABLE HUMAN WASTE MANAGEMENT DEVICE WITH IMPROVED ADHESIVE FOR SKIN ATTACHMENT

FIELD OF THE INVENTION

The present invention relates to a disposable human waste management devices such as urine management devices and faecal management devices for babies, children or adults to be attached directly to the skin between the buttocks of the wearer. The device utilises an improved adhesive so as to facilitate easy application and removal of the device from the wearer, whilst ensuring maintenance of the device in the desired position.

BACKGROUND OF THE INVENTION

Urine and faecal management devices are known articles of manufacture that are designed to be worn principally by incontinence sufferers and in particular by bedridden patients. Such devices are attached to the natural anal region or artificial anus of the wearer and/or uro-genital area and are intended to receive, entrap and immediately contain urine, faecal material and other bodily discharges.

Such devices as they are mostly known today are designed to be worn by bedridden patients. As such the devices are constituted of a relatively long and narrow tube, at one extremity of which there is an aperture and a skin attachment device upon which an adhesive can be applied.

Examples of these bags are disclosed for example in U.S. Pat. No. 3,577,989, which details a disposable elimination-trapping bag for incontinence sufferers including a container member having an open-top portion, and a flange secured to the container member around the open-top portion. The flange may include a layer of adhesive on its surface as a means of attachment of the bag to the wearer or alternatively discloses the use of elastic straps to attach the bag to the wearer. U.S. Pat. No. 4,784,656 also describes a receptacle for collecting faecal matter from incontinence sufferers. The faecal collector comprises a gasket, conduit means or a cylinder and a receptacle; the receptacle and conduit means are each formed from two sheets of odour barrier thermoplastic film that are heat sealed along their side edges, respectively and the side surface of the gasket is coated with a layer of adhesive. GB 2 152 387, teaches a faecal collector for incontinence sufferers comprising a collection bag and a ring, which is provided with an adhesive. The faecal collector comprises a pair of panels of thermoplastic sheet material joined at their margins to define an elongate bag having an opening at one end. GB 1 078 588 describes a urine collector comprising a liquid proof bag of tube-like configuration having an opening surrounded by an attachment means in the form of an adhesive bearing material.

Other types of faecal management bags having a flatter shape are known from EP 245 064. EP 245 064 discloses bags having a front and a rear wall, the front wall containing the aperture and attachment means to the body. The attachment means is a skin compatible water resistant material such as a hydrocolloid and a water insoluble viscose elastic binder.

Due to their typical elongated shape and dimensions, such devices particularly when worn by active wearers, such as infants or non bedridden incontinent adults, can readily twist around the thighs of the wearers and/or can cause the formation of folds and kinks in the devices themselves. Under such circumstances the pressure and stress exerted upon the bag will naturally increase due to the movement of the wearer and the pressure of the wearer's body upon the bag. Consequently, the likelihood that the urine or faecal material once excreted and contained within the bag will be caused to exert pressure upon the attachment means of the device will increase. As a result not only will the storage capacity of the device be detrimentally affected but also more importantly it may result in unintentional detachment of the device from the wearer during use. Such an occurrence is unacceptable causing distressing consequences for both the wearer and the carer.

Hence, it is critical that the urine and/or faecal management devices are designed such that they are securely attached to the skin of the wearer and do not become unintentionally unattached during all circumstances of use.

In order to provide the desired level of adhesion of the device to the wearer, the prior art typically discloses the utilisation of certain adhesives having very high cohesive strengths such as rubber based adhesives and acrylics. These adhesives are then applied as thick layers over the entire surface of the flange of the device to maximise the adhesive force by which the device is secured to the skin of the wearer. Indeed it is apparent that these devices, and in particular the adhesives, have been designed for use on faecal management devices utilised by bedridden patients particularly those having an artificial anus whereby maximum adhesion takes priority over any other criteria such as patient comfort.

However, the adhesive must have a skin compatible composition and not be harsh or aggressive towards the skin or cause skin irritation or inflammation. Also it is preferred if the adhesive is compliant with the-skin of the wearer such that maximum skin surface contact between the adhesive and the skin is achieved. Moreover, it is also desirable to provide an adhesive such that the disposal human waste management device can be readily removed from the wearer, without the wearer experiencing any unacceptable pain level. This is particularly important under circumstances, where the device is misplaced and removal and reapplication of the device once or even a number of times is required and or to ensure the application of such devices on sensitive skin and wearer groups such as infants. However, on the other hand the desired level of adhesion, albeit painless should of course also be maintained during such multiple applications of the device.

Hence there exists a need to provide disposable human waste management devices having an adhesive for the secure attachment and painless removal of the device from the skin between the buttocks of the wearer so as to be suitable for use of sensitive skin of an infant and it is thus an object of the present invention to provide such a device.

It is another objective of the present invention to provide an adhesive that exhibits an ability to adhere to skin upon reapplication, particularly multiple reapplication for example when the device is misplaced, whilst still allowing painless removal.

An additional object of the present invention is to provide an adhesive which in combination with the flange material provides flexibility, stretchability and contractability so that it is able to adapt to the contours of the body during all bodily movements and hence be comfortable for the wearer of the device, whilst still having sufficient adhesive capacity to ensure secure attachment during use.

In addition to the above objectives of the present invention it is also desirable for the adhesives to provide additional benefits such as delivery/dispersal of a compound or composition which is beneficial for the skin or for the body in general.

It has now been surprisingly found that the above drawbacks will be substantially alleviated by providing the flange of the disposal human waste management device with an adhesive as defined hereinafter. The adhesive provides secure attachment, is pleasing to the skin upon application, and yet causes no discomfort upon removal and maintains its adhesive strength over the period of wear.

In another aspect of the present invention, the disposal human waste management device with its specific adhesive as defined herein can be advantageously used in combination with a reusable underwear garment or preferably with a disposable diaper.

SUMMARY OF THE INVENTION

According to the invention there is provided a disposable human waste management device in association with the adhesive as defined herein. Typically urine and faecal management devices comprise a bag (11) having an aperture (21) and a flange (12) surrounding the aperture for adhesive attachment to the uro-genital area and or the perianal area of a wearer as visible from FIG. 1.

The adhesive allows attachment of disposable human waste management devices to the skin of the wearer, the adhesive being provided as a layer having a certain thickness or calliper C measured in millimetres (mm), typically on at least part of the wearer facing surface of the flange.

Detailed analysis of the sequence of common situations occurring from the application of a faecal management device to the time of removal of such a device has shown that specific adhesive characteristics need to be preferably satisfied in order to achieve the desired performance objectives, in particular to secure initial attachment, secure attachment during use and painless removal after wear. The characteristics which have been considered in this context are the elastic modulus describing the elastic behaviour of the material and the viscous modulus which describes the viscous behaviour of the adhesive material.

The viscous behaviour of the adhesive can be interpreted to represent an indication of the ability of the adhesive to quickly attach and securely adhere to a particular surface. The elastic behaviour can be interpreted as an indication of the "hardness" behaviour of the adhesive. Its value is also important for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

In order to provide topical adhesives for secure initial and prolonged attachment and easy/painless removal the relation between the elastic modulus and the viscous modulus as well as their dynamic behaviour is also of importance.

The adhesive has an elastic modulus at a temperature of 37° C. (1.00° Fahrenheit) abbreviated $G'_{37}$, a viscous modulus at a temperature of 37° C. (100° Fahrenheit) of $G''_{37}$, and a viscous modulus at a temperature of 25° C. (77° Fahrenheit) of $G''_{25}$.

The adhesive used in the present invention preferably satisfies the following conditions;

$G'_{37}$ (1 rad/sec) is in the range 500 Pa to 20000 Pa, preferably 700 Pa to 15000 Pa, most preferably 1000 Pa to 10000 Pa.

$G''_{37}$ (1 rad/sec) is in the range 100 Pa to 15000 Pa, preferably 100 Pa to 10000 Pa, most preferably 300 Pa to 5000 Pa.

and the ratio of $G'_{37}$ (1 rad/sec)/$G''_{37}$ (1 rad/sec) is in the range of 1 to 30.

Provided the above Theological conditions are satisfied the adhesives will also satisfy conditions such as sufficient cohesiveness (to prevent residue of adhesive on the skin) which are important for commercial use of such adhesives and apparent to those skilled in the art. Adhesive compositions which satisfy the above criteria can be used as adhesives for the flange provided they also satisfy the common requirements of being safe for use on human or animal skin during use and generally after disposal of the device.

Often the criteria of hygienic appearance such that adhesive compositions which are transparent or white upon application are preferred.

It has been determined that the relation between the thickness or calliper C, measured in millimetres (mm), of the layer in which the adhesive is provided, typically onto at least a portion of the wearer facing surface of the flange, and the viscous modulus $G''_{25}$ at about 100 rad/sec of the adhesive, is relevant to the scope of providing an easy and painless removal from the wearer's skin of such a adhesive applied on at least part of the wearer facing surface of a faecal management device for attachment of said device to the skin of a wearer.

The adhesive used in the present invention is thus preferably provided as a layer having a thickness C such that the viscous modulus $G''_{25}$ (100 rad/sec) and the thickness C preferably satisfy the following empirical equation:

$$G''_{25} \leq [(7.00+C) \times 3000]\, Pa$$

and preferably also the following empirical equation:

$$G''_{25} \leq [(5.50+C) \times 1700]\, Pa$$

DETAILED DESCRIPTION OF THE INVENTION

Figure 1:
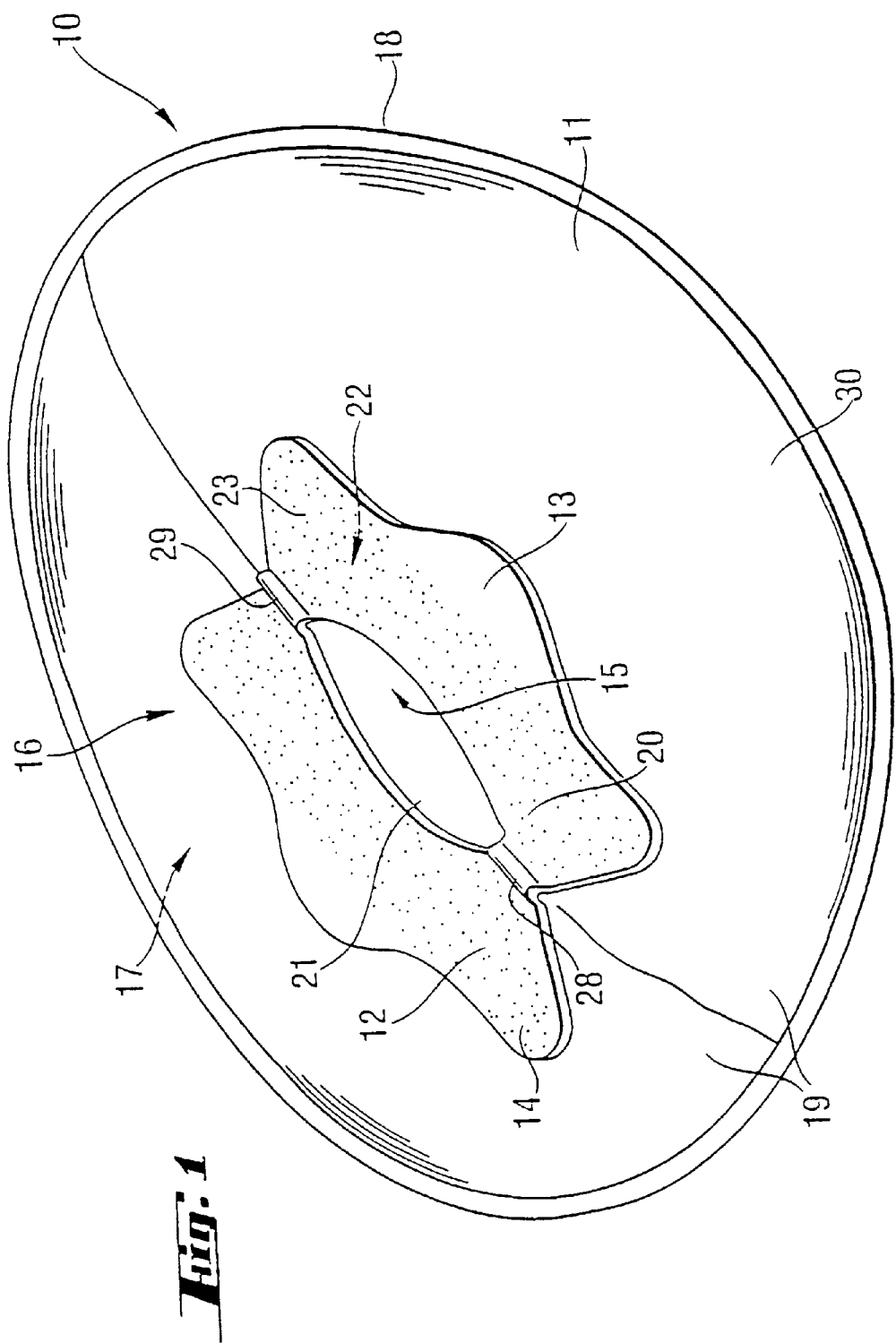
FIG. 1 is a perspective view of a disposable faecal management device in accordance with the present invention.

According to the present invention the adhesive can be utilised on disposable human waste management devices such as a faecal or urine management devices (10) which are applied to the perianal area of a wearer as visible from FIG. 1. The word "skin" according to the present invention does not only relate to the specific derma of the user but includes the mucous tissue as well as the hair which is typically found in the genital region.

The adhesive is provided with the preferred pattern, typically on the wearer facing surface (23) of the flange (12) of the device (10), as a layer having a thickness or calliper C that is preferably constant. The layer can be preferably continuous or alternatively discontinuous, e.g. in form of dots, spirals, or stripes.

Even though adhesives are used like pressure sensitive adhesives on human skin hair and mucous tissues, it is understood that the adhesive compositions could only with difficulty be considered typical pressure sensitive adhesives (referred to as PSA hereinafter) on the basis of the most characteristic Theological behaviours identifying such materials.

In fact as the person skilled in the art of adhesives knows, the most characteristic feature that distinguishes a PSA from other substances that can temporarily adhere objects (e.g. water between two glass plates could) is the fact that their rheological parameters and especially the Elastic Modulus G' vary greatly with the frequency of applied stresses. More in particular, G' of PSA can increase over some orders of magnitude, while the frequency of applied stresses varies from typical bonding frequency to typical debonding frequency, i.e. 1 rad/s to 100 rad/s as indicated below.

As a first consequence, it is therefore inadmissible to define materials intended for use as "adhesives" by giving values of rheological parameters and especially of G' at a fixed value of frequency. This can be misleading because in the absence of other characteristics such as surface chemistry it will include materials which have no practical value. It is hence necessary that rheological characterisation must be on the basis of dynamic considerations. This not only applies to the Elastic Modulus G' but also to the viscous modulus G" and hence also for tan (d)=G"/G'.

It is well known that typical PSAs have not only a high variation of G' across the considered frequencies, but also that there is an even higher variation of G" which can get close or become even higher than the value of G', i.e. tan (d) becomes about or even greater than 1, in particular at the frequencies that are typical of debonding.

Without wishing to be bound by theory this can be interpreted as meaning that a high fraction of the energy applied for the debonding is dissipated within the adhesive (so it is not effective in causing the debonding) and through the interface of the adhesive and the skin, while this fact causes macroscopically the recording of a very high level of adhesive force.

As indicated above materials useful as adhesives for use in the present invention have rheological characteristics which are measured at a reference temperature of 37° C. (as usual body temperature of humans) and in a range of frequencies. It has been found that upon application of a human waste management device with an adhesive, the adhesive contact is formed at a low frequency, while debonding happens at the speed of removing the device. This speed is expressed as a frequency of 100 rad/s, while the low frequency of forming the adhesive bond has been found to be on the order of 1 rad/s. Therefore, the frequency range for use according to the present invention is between 1 and 100 rad/s.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion while the material remains soft and capable of gently adhering to skin.

The ratio of $G'_7$ (1 rad/sec) over $G''_{37}$ (1 rad/sec) is important to ensure that these two values are balanced upon adhesion to the skin. importantly, the ratio of $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

needs to be large enough to ensure that the dynamic behaviour of both the elastic and the viscous module are maintained in a relationship which provides secure adhesion and painless and easy removal.

Finally the person skilled in the art will also recognise that the Glass Transition Temperature Tg of the adhesive composition, the specific heat capacity, and the specific heat conductivity are parameters which are useful to more fully define the group of useful adhesives.

The following set of characteristics should preferably be satisfied for the adhesive for use in the present invention:

| | |
|---|---|
| $G'_{37}$ (1 rad/sec) | is in the range 500 Pa to 20000 Pa, preferably 700 Pa to 15000 Pa, most preferably 1000 Pa to 10000 Pa. |
| $G''_{37}$ (1 rad/sec) | is in the range 100 Pa to 15000 Pa, preferably 100 Pa to 10000 Pa, most preferably 300 Pa to 5000 Pa. |
| the ratio of $G'_{37}$ (1 rad/sec)/ $G''_{37}$ (1 rad/sec) is in the range of 1 to 30. | |
| the ratio | $\frac{G'_{37}(100 \text{ rad/sec}) - G''_{37}(100 \text{ rad/sec})}{G'_{37}(1 \text{ rad/sec}) - G''_{37}(1 \text{ rad/sec})}$ is not less than 0.5, preferably in the range 0.7 to 3, most preferably in the range 1 to 1.8. |

The value of the ratio of $G'_{37}/G''_{37}$ at least for the frequency range above 1 rads/up to 100 rads/s should preferably be not less than 0.5, preferably from 0.7 to 10 and most preferably from 1 to 7.

The rheological behaviour can also be related to the values of the Glass Transition Temperature Tg. For topical adhesives for use in the present invention Tg should preferably be less than 0° C., more preferably less than −5° C. and most preferably less than −10° C.

In order to provide adhesive compositions which satisfy the requirements of the above rheological and physical characteristics of an adhesive any medically suitable substantially water insoluble pressure sensitive adhesives comprising a polymer which forms a 3-dimensional matrix meeting the these characteristics may be utilised.

According to the present invention the 3 dimensional matrix also referred to herein as a gel, comprises as an essential component a polymer which can be physically or chemically cross linked. The polymer may be naturally or synthetically derived. The uncrosslinked polymer includes repeating units or monomers derived from vinyl alcohols, vinyl ethers and their copolymers, carboxy vinyl monomer, vinyl ester monomers, esters of carboxy vinyl monomers, vinyl amide monomers, anionic vinyl monomers, hydroxy vinyl monomers, cationic vinyl monomers containing amines or quaternary groups, N-vinyl lactam monomer, polyethylene oxides, polyvinylpyrrolidone (PVP), polyurethanes, acrylics such as methyl acrylate, 2-hydroxyethyl methacrylate, methoxydiethoxyethyl methacrylate and hydroxydiethoxyethyl methacrylate, acrylamides,and sulphonated polymers such as acrylamide sulphonated polymers for example 2 acrylamido methylpropane sulphonic acid and acrylic (3-sulphopropyl) ester acid, and mixtures thereof. Also acrylonitrile, methacrylamide, N,N,-dimethylacrylamide, acrylic esters such as methyl, ethyl and butyl acrylates. Alternatively, the uncrosslinked polymer may be a homopolymer or copolymer of a polyvinyl ether, or a copolymer derived from a half ester of maleic ester. Similarly any other compatible polymer monomer units may be used as copolymers such as for example polyvinyl alcohol and polyacrylic acid or ethylene and vinyl acetate.

As another alternative, the polymers may be block copolymer thermoplastic elastomers such as ABA block copolymers such as styrene-olefin-styrene block copolymers or ethylene-propylene block copolymers. More preferably such polymers include hydrogenated grade styrol/ethylene-butylene/styrol (SEBS), styrene/isoprene/styrene (SIS), and styrol/ethylene-propylene/styrol (SEPS).

Particularly preferred polymers are acrylics, sulphonated polymers such as acrylamide sulphonated polymers, vinyl alcohols, vinyl pyrrolidone, polyethylene oxide and mixtures thereof. Most preferred are nitrogen containing polymers.

According to the present invention the 3 dimensional adhesive matrix also essentially comprises a plasticiser, which is preferably a liquid at room temperature. This material is selected such that the polymer may be solubilized or dispersed within the plasticiser. For embodiments wherein irradiation cross linking is to be carried out, the plasticiser must also be irradiation cross linking compatible such that it does not inhibit the irradiation cross linking process of the polymer. The plasticiser may be hydrophilic or hydrophobic.

Suitable plasticisers include water, alcohols, polyhydric alcohols such as glycerol and sorbitol, and glycols and ether glycols such as mono- or diethers of polyalkylene gylcol, mono- or diester polyalkylene glycols, polyethylene glycols (typically up to a molecular weight of about 600), glycolates, glycerol, sorbitan esters, esters of citric and tartaric acid, imidazoline derived amphoteric surfactants, lactams. amides, polyamides, quaternary ammonium compounds, esters such phthalates, adipates, stearates, palmitates, sebacates, or myristates, and combinations thereof. Particularly preferred are polyhydric alcohols, polyethylene glycol (with a molecular weight up to about 600), glycerol, sorbitol, water and mixtures thereof.

Typically the adhesive comprises a ratio of polymer to plasticiser by weight of from 1:100 to 100:1, more preferably from 50:1 to 1:50. However, the exact amounts and ratios of the polymer and plasticiser will depend to a large extent on the exact nature of polymer and plasticisers utilised and can be readily selected by he skilled person in the art. For example a high molecular weight polymer material will require a greater amount of plasticiser than a low molecular weight olymer.

Other common additives known in the art such as preservatives, antioxidants, pigments, mineral fillers and mixtures thereof may also be comprised within the adhesive composition in quantities up to 10% by weight each respectively.

According to the present invention the polymer component of the adhesive can be physically or chemically cross linked in order to form the 3 dimensional matrix. Physical cross linking refers to polymers having cross links which are not chemical covalent bonds but are of a physical nature such that there are areas in the 3 dimensional matrix having high crystallinity or areas having a high glass transition temperature. Chemical cross linking refers to polymers which are linked by chemical bonds. Preferably the polymer is chemically cross linked by radiation techniques such as thermal-, E beam-, UV-, gamma or micro-wave radiation.

In addition when chemical crosslinks are formed in the system, a polyfunctional cross linker and/or a free radical initiator may be present in the premix to initiate the crosslinking upon irradiation. Such an initiator can be present in quantities up to 5% by weight, preferably from 0.02% to 2%, more preferably from 0.02% to 0.2%. Suitable photoinitiators include type I-α-hydroxy-betones and benzilidimethyl-betols e.g. Irgacure™ 651 which are believed to on irradiation to form benzoyl radicals that initiate polymerization. Particularly preferred is I-hydroxycyclohexylphenylketone (available under the trade name Irgacure™ 184 from Ciba Specialty Chemicals). In addition from 0.02% to 2% of thermal initiators may also be used.

The performance of hydrogels as adhesives is related to the surface energetics of the adhesive and of the adherend (for example mammalian skin) and to the viscoelastic response of the bulk adhesive. The requirement that the adhesive wets the adherend to maximise the work of adhesion is well known. This requirement is generally met when the adhesive has a similar or lower surface energy to the adherend. The viscoelastic properties, in particular the elastic or storage modulus (G') and the viscosity modulus (G") are important. They are measured by dynamic mechanical testing at different rad/s. Their values at low rad/s (approximately 0.01 to 1 rad/s) and high rad/s (100 to 1000 rad/s) has been related to the wetting/creep behaviour and peel/quick stick properties respectively. The choice, assembly and processing of the ingredients of the hydrogel adhesive are usually targetted at making a material with a balance of properties suitable for pressure sensitive adhesive applications. A balance between the quantities and nature of polymer, plasticiser and the degree of crosslinking/entanglement has to be achieved.

When water is lost from the hydrogel the adhesive properties are likely to change deleteriously. Whilst the presence of glycerol or other polyhydric alcohols in other reported formulations has been quoted to provide humectant properties to the hydrogel, it has been found that the most important parameter to preventing water loss is the activity of the water within the hydrogel which in turn depends on the nature and proportions of the other components and manner of processing.

Water activity in the hydrogel adhesive is primarily dependent on the water content and the nature of the polymeric components and the way in which they are processed. Water activity has been shown to have a better correlation with the growth of bacteria and moulds than water content. It has been found that organisms struggle to grow at water activities less than 0.8. Enzyme activity has also been reported to decrease significantly below activity of 0.8. Water activity has also been found to influence the adhesivity of the hydrogel adhesive in that at water activities above about 0.75, they become less adhesive. A bioadhesive composition having a suitable balance of the characteristics discussed above has now surprisingly been found.

According to the invention there is provided a bioadhesive composition characterised in that it has:
 (i) a water activity of from 0.4 to 0.9;
 (ii) an elastic modulus at 1 rad/s of from 700 to 15,000 Pa;
 (iii) an elastic modulus at 100 rad/s of from 2000 to 40,000 Pa;
 (iv) a viscous modulus at 1 rad/s of from 400 to 14,000 Pa;
 (v) a viscous modulus at 100 rad/s of from 1000 to 35,000 Pa;
wherein the viscous modulus is less than the elastic modulus in the frequency range of from 1 to 100 rad/s.

Examination of the rheological properties of the compositions have been successfully used to characterise and differentiate adhesive behaviour. Typically the elastic modulus (G') and the viscous modulus (G") are measured over a range of 0.01–100 rad/s at a given temperature. For skin applications the appropriate temperature is 37° C. The moduli at low rad/s values relate to the initial bonding of the adhesive to skin and the higher to the changes in moduli values associated with de-bonding. Methods of measuring G' and G' are well known; for example a Rheometric Scientific, Inc. model RS-5 rheometer could be used.

The water activity of the composition can be measured using impedance methods with devices such as the Rotronic, Inc. AWVC. The activity of water may also be determined by placing the composition in environments of controlled humidity and temperature and measuring the changes in weight. The relative humidity (RH) at which the composition does not change weight corresponds to the activity of water in the gel (RH/100). The use of saturated salt solutions to provide the appropriate environmental conditions is well known. All compositions directly exposed to relative humidities less than that corresponding to the activity of water will be thermodynamically allowed to lose water. Exposure to greater relative humidities and the composition will gain weight.

The bioadhesive composition preferably comprises an aqueous plasticiser, a copolymer of a hydrophilic unsaturated water-soluble first monomer and a hydrophilic unsaturated water-soluble second monomer and a cross-linking agent, the first monomer being capable of enhancing the bioadhesive properties of the composition.

Preferably the first monomer can enhance the mechanical strength of the composition and/or the second monomer can increase the water activity of the composition.

The bioadhesive composition is preferably prepared by polymerising an aqueous reactive mixture comprising the said first monomer, the said second monomer and a crosslinking agent.

According to the invention there is further provided a biomedical electrode which comprises a bioadhesive composition in association with an electrically conductive interface. Optionally, the biomedical electrode can also further comprise a support. The electrically conductive interface preferably comprises a layer of electrically conductive material which is preferably applied to the support, when present.

The invention also provides a fixation product suitable for attaching a biomedical device to skin (or the human body) e.g. a catheter, tubing, wires or cables which product comprises a bioadhesive composition.

In preferred embodiments the first and second monomers will be acrylate based monomers selected for their ability to polymerise rapidly in water and having substantially the same molecular weight whereby in a mixture of the two the relative proportions may be varied without significantly altering the molar characteristics of the composition.

The first monomer is preferably a compound of the formula

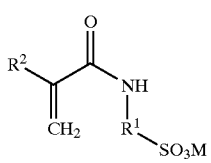

(I)

wherein $R^1$ a substituted hydrocarbon moiety, $R^2$ is hydrogen or a substituted methyl and/or substituted ethyl, and M represents hydrogen or a cation.

$R^1$ is preferably a substituted alkyl, cycloalkyl or aromatic moiety. Preferably $R^1$ represents a saturated moiety or an aromatic moiety. $R^1$ preferably contains from 3 to 12 carbon atoms, more preferably from 3 to 6 carbon atoms. A preferred moiety which $R^1$ represents is

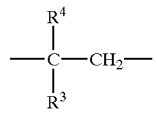

wherein $R^3$ represents hydrogen or a substituted straight or branched chain alkyl group possessing from 1 to 6 carbon atoms and $R^4$ represents a substituted straight or branched chain alkyl group possessing from 1 to 6 carbon atoms.

The second monomer is preferably a compound of formula

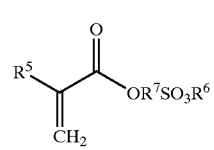

(II)

wherein $R^5$ represents hydrogen or a substituted methyl and/or substituted ethyl, $R^6$ represents hydrogen or a cation and $R^7$ represents a substituted alkyl moiety of 1 to 4 carbon atoms. Preferably $R^7$ represents a substituted n-propyl.

$R^1, R^2, R^3, R^4, R^5$ and $R^7$ are substituted by a group which preferably has a tendency to increase the water solubility of the compound. Suitable groups will be well known to a person of skill in the art. A preferred substituent is a hydroxyl, amino or ammonium group or a halogen (e.g. chlorine, bromine, or iodine) atom. A suitable cation is an alkali metal cation, especially sodium or potassium.

Most preferably the first monomer is 2-acrylamido-2-methylpropanesulphonic acid or an analogue thereof or one of its salts, e.g. an alkali metal salt such as a sodium, potassium or lithium salt, while the second monomer is a polymerisable sulphonate or a salt, e.g. an alkali metal salt such as a sodium, potassium or lithium salt, of acrylic acid (3-sulphopropyl)ester or an analogue thereof. Particular preferred examples of these respective monomers are the sodium salt of 2-acrylamido-2-methylpropanesulphonic acid, commonly known as NaAMPS, and acrylic acid (3-sulphopropyl)ester potassium salt, commonly known as SPA. NaAMPS is available commercially at present from Lubrizol as either a 50% aqueous solution (reference code LZ2405) or a 58% aqueous solution (reference code LZ7405A). SPA is available commercially in the form of a solid from Raschig.

The total monomer content in the aqueous reactive mixture is preferably from 15% to 60% by weight, preferably from 20% to 50% by weight.

In preferred embodiments the ratio by weight of the first monomer to the second monomer is from 20:1 to 2:3, preferably 10:1 to 2:3; more preferably in the range 60:40 to 40:60, and may sometimes be approximately 50:50.

The first monomer is preferably included in an amount by weight of from 1% to 60%, more preferably from 5% to 50%, most preferably from 15% to 40%. The second monomer is preferably included in an amount by weight of from 1% to 50%, preferably from 10% to 30%, most preferably from 10% to 20%. The crosslinker is preferably included in an amount of from 0.01% to 2%, more preferably from 0.1 to 2% by weight. The balance of the composition preferably comprises an aqueous plasticiser.

One advantage of the first and second monomers is that it has been found that high monomer content solutions can be achieved (approximately 75%). It has also been found that the second monomer is soluble in polyhydric alcohols such as glycerol, and addition of glycerol to the first and second monomer mixture enhances the solubilisation process. It has been found that the combination of the two monomers enables a greater control over water content than can be achieved otherwise. This can be important because it has also been found that compositions made with the final water content as an integral part of the pre-gel mix have different properties from those made with an excess of water and then dried to the final composition. For example, hydrogels with a final composition obtained by the evaporation of water generally have lower elastic or storage moduli than those made with no evaporation of water. To obtain similar levels of elastic moduli, the amount of crosslinker required in the former materials is higher. The evaporation of water and extra crosslinker add to the cost of the process. This problem is avoided by the present invention where a final drying step is generally not required.

Conventional crosslinking agents are used to provide the necessary mechanical stability and to control the adhesive properties of the composition. Although compositions can be made with suitable adhesive and electrical properties, a sufficient amount of a suitable cross-linker must be used; if too little crosslinker is used, converting the material into a completed electrode becomes impossible. Typical crosslinkers include tripropylene glycol diacrylate, ethylene glycol dimethacrylate, alkoxylated triacrylate, polyethylene glycol diacrylate (PEG400 or PEG600), methylene bis acrylamide.

The aqueous reactive mixture can further comprise a surfactant, an additional monomer, a processing aid (which is preferably a hydrophobic polymer), a water soluble polymer suitable for forming an interpenetrating polymer network, a non-hydrophilic polymer, and/or an antimicrobial agent (e.g. citric acid, stannous chloride).

The process used to prepare bioadhesive compositions in accordance with the invention comprises mixing the ingredients to provide a reaction mixture in the form of an initial pre-gel aqueous based liquid formulation, which is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer an siliconised release paper or other solid substrate. The processing will generally be carried out in a controlled manner involving a precise predetermined sequence of mixing and thermal treatment or history. One preferred feature of the process according to the invention is that no water is removed from the hydrogel after manufacture.

Additional Monomer

The composition according to the invention preferably comprises one or more additional monomers. A suitable additional monomer is a non-ionic monomer or ionic monomer. If the monomer is ionic, it is either anionic or cationic. Additional monomers, when present, are preferably included in an amount of up to 10% by weight.

A preferred non-ionic monomer is a N-disubstituted acrylamide (preferably an N,N-dialkylacrylamide) or an analogue thereof. N,N-dimethylacrylamide (NNDMA) t and/or an analogue thereof is particularly preferred.

A preferred cationic monomer is a quaternary ammonium salt. An especially preferred cationic monomer is (3-acrylamidopropyl)trimethyl ammonium chloride or [2-(acryloyloxy)ethyl]trimethyl ammonium chloride.

A preferred anionic monomer is an acrylate based monomer such as acrylic acid or a salt or ester thereof.

Plasticiser

The compositions according to the invention generally comprise, in addition to a crosslinked polymeric network, an aqueous plasticising medium and, optionally, additional electrolyte. Plasticisers are generally used in the invention to control adhesive properties.

The aqueous plasticising medium can additionally comprise a polymeric or non-polymeric polyhydric alcohol (such as glycerol), an ester derived therefrom and/or a polymeric alcohol (such as polyethylene oxide). Glycerol is the preferred plasticiser. An alternative preferred plasticiser is an ester derived from boric acid and a polyhydric alcohol (such as glycerol). The aqueous reactive mixture preferably comprises from 10% to 50%, preferably from 10% to 45%, of plasticiser (other than water) by weight of the mixture.

It is well known that water in hydrogels can be present in at least two forms, freezing and non-freezing, as measured by Differential Scanning Calorimetry. In many examples of commercially available hydrogels the water is present only as non freezing water. It has been found, however, that compositions with useful adhesive properties comprising the first and second monomers can be made which have both freezing and non-freezing water, and the water activity in such gels is generally high. One advantage of including the second monomer is that it has a tendency to increase the likelihood that the compositions will contain freezing water. The advantage gained by the presence of freezing water becomes evident in the application of these gels to stress monitoring ECG. In certain cases the preferred medium for interfacing the monitoring instrument with the body is a "wet gel". It has been suggested that the advantage gained by "wet gels" is in the wetting of the skin and consequent lowering of skin impedance, but it has been found in clinical trials that hydrogels with freezing water can match the performance of "wet gels".

Internenetrants

The compositions preferably additionally comprise a water soluble polymer suitable for forming an interpenetrating polymer network. Hydrogels based on interpenetrating polymer networks (IPN) are well known. An IPN has been defined as a combination of two polymers, each in network form, at least one of which has been synthesised and/or crosslinked in the presence of the other. As will be appreciated, this combination will generally be a physical combination rather than a chemical combination of the two polymers. IPN systems may be described by way of example as follows:

Monomer 1 is polymerised and crosslinked to give a polymer which is then swollen with monomer 2 plus its own crosslinker and initiator.

If only one polymer in the system is crosslinked the network formed is called a semi-IPN. Although they are also known as IPN's, it is only if there is total mutual solubility that full interpenetration occurs. In most IPN's there is, therefore, some phase separation but this may be reduced by chain entanglement between the polymers. It has also been reported that semi IPN's can be made in the presence of carrier solvents (for example water in the case of hydrophilic components).

It has been found that polymerising and crosslinking water soluble monomers in the presence of water soluble polymers, water and polyhydric alcohols produce hydrogel materials with enhanced rheological and consequently adhesive properties.

Suitable water soluble polymers for the formation of semi IPN's include poly (2-acrylamido-2-methylpropanesulphonic acid) or one of its salts and its copolymers, poly (acrylic acid-(3-sulphopropyl) ester potassium salt), copolymers of NaAMPS and SPA, polyacrylic acid, polymethacryiic acid, polyethylene oxide, polyvinyl methyl ether, polyvinyl alcohol, polyvinylpyrrolidone, its copolymers with vinyl acetate, dimethylaminoethyl methacrylate, terpolymers with dimethylaminoethyl methacrylate and vinylcaprolactam, polysaccharides such as gum arabic, karaya gum, xanthan gum, guar gum, carboxymethyl cellulose (CMC), NaCMC, hydroxypropylmethyl cellulose (HPMC), hydroxyethyl cellulose (HEC) or combinations thereof.

In The amount of interpenetrant polymer used will be dependent on the mechanical and rheological properties required as well on consideration of processing conditions. If the interpenetrant polymer used increases the viscosity of the pre-gel mix beyond 5000 centipoise it has been found that the monomers do not polymerise and crosslink on an acceptable time scale (should be less than 60 seconds, preferably less than 10 seconds). The viscosity depends on the nature and molecular weight of the interpenetrant and the nature of pre-gel processing.

Of the natural polysaccharides, gum arabic or maltodextrin is usually preferred due to its cold water solubility and lesser effect on viscosity compared with, for example, karaya gum. A higher concentration of gum arabic than karaya may therefore be used if desired, enabling a wider control of hydrogel properties. It has also been found that the processing steps for assembling the pre-gel formulation can be critical with respect to the properties of the manufactured hydrogel. For a given formulation, if the components are assembled at 25° C. and cured different electrical and adhesive properties are obtained compared to those that have been heated to 70° C. Whilst adhesive properties may be enhanced, electrical properties e.g. low frequency impedance, can be downgraded. Solutions containing natural polysaccharides become less opaque indicative of improved solubility. The activity of water in compositions prepared from heat treated pre-gels generally is lower than in non heat treated pre-gels.

Other additives

The composition preferably comprises a hydrophobic polymer and/or a lipid micellizing polymer. Hydrophobic polymers may be incorporated either in the presence or absence of interpenetrant polymers to form phase separated materials. The preparation of two phase composites consisting of a hydrophilic polymer containing an ionically conducting continuous phase and domains of a hydrophobic pressure sensitive adhesive which enhance adhesion to mammalian skin have been reported in U.S. Pat. No. 5,338,490. The method of preparation described therein involved casting a mixture (as a solution and or suspension) consisting of the hydrophilic polymer containing phase and hydrophobic components onto a substrate and then removing the solvent. It has been found, however, that adhesive ionically conducting hydrogels may be better prepared by combining the hydrophobic polymer (preferably as an emulsion) with the components of the pre-gel reaction mixture and casting these onto a substrate and curing. In other words, there is no need to remove a solvent in order to form useful materials. Furthermore, the hydrophilic phase of the composition in addition to being a crosslinked network may also be an IPN or semi IPN.

It is believed that when hydrophobic polymers are incorporated in this way that the hydrophobic component segregates to the surface (as determined by Fourier transform infrared attenuated total reflectance spectroscopy, FTIR ATR, approximate sampling depth 1 $\mu$m using a ZnSe crystal or 0.25 $\mu$m with a Germanium crystal) and that it is the amount of the hydrophobic component present in the surface that influences the adhesion to a wide variety of materials the greater the amount of the hydrophobic component in the surface the greater the adhesion. In U.S. Pat. No. 5,338,490 weight ratios of the hydrophilic phase to the hydrophobic phase of 60:1 to 8:1 were claimed. In hydrogel adhesives of between 100 to 2000 microns thick made in accordance with the present invention, ratios of hydrophilic to hydrophobic components ranging from 7:1 to 1:20 have been found to be preferable, especially when these ratios are present in the surface of the adhesive composition. In the process of the present invention, however, it may take up to 72 hours from the initial curing of the adhesive hydrogel for the segregation of the hydrophobic materials to the surface, as defined by the ATR sampling depth, to be complete.

Preferably, the hydrophobic pressure sensitive adhesive in such embodiments is selected from the group consisting of polyacrylates, polyolefins, silicone adhesives, natural or synthetically derived rubber base and polyvinyl ethers or blends thereof. Preferably the hydrophobic pressure sensitive adhesive in these embodiments is an ethylene/vinyl acetate copolymer such as that designated DM137 available from Harlow Chemicals or vinyl acetate dioctyl maleate such as that designated Flexbond™ 150 and sold by Air Products. Those skilled in the art will also know that the molecular weight and comonomer ratios may be altered to control the properties of hydrophobic pressure sensitive adhesives. In general, the degree of surface segregation exhibited by such hydrophobic pressure sensitive adhesive (HPSA) will be dependent on factors such as composition of the HPSA, viscosity of the pre-gel mixture, temperature and rate of curing.

Surfactant

The composition according to the invention optionally includes a surfactant.

Any compatible surfactant may be used. Nonionic, anionic and cationic surfactants are preferred, either alone or in combination. The surfactant is preferably included in an amount from 0.1% to 20% by weight, more preferably 0.1% to 10% by weight.

In certain circumstances the reaction mixture preferably comprises from 3% to 20%, and more preferably from 8% to 18% by weight of the reaction mixture, of a stabilised polymer dispersion that is used to provide a stable phase separated system. The polymer preferably comprises any of the following either alone or in combination: vinylacetate dioctyl maleate copolymer or ethylene-vinyl acetate copolymer. Ethylene-vinylacetate copolymer is preferred, such as that marketed under the trade name DM137 by Harlow Chemicals.

The adhesive is thus typically formed by polymerising an aqueous reaction comprising from 5 to 50%, preferably from 30% to 50% by weight of the reaction mixture, of hydrophilic monomer, i.e. an ionic water soluble monomer, from 10% to 50%, preferably from 15% to 45% by weight of the reaction mixture, of a plasticiser (other than water), from 10% to 50%, preferably from 15% to 30% more preferably from 15% to 25% by weight of the reaction mixture, of a hydrophobic nonionic monomer, i.e. nonionic water soluble monomer, from 3 to 40%, by weight of the reaction mixture, of water.

In preparing adhesive compositions for use in the invention, the ingredients will usually be mixed to provide a reaction mixture in the form of an initial pre-gel aqueous based liquid formulation, and this is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer on siliconised release paper or other solid substrate. The incident UV intensity, at a wavelength in the range from 240 to 420 nm, is ideally substantially 40 mW/cm². The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers and for conversion better than 99.95% exposure to UV light less than 60 seconds and preferably less than 40 seconds is preferred. Those skilled in the art will appreciate that the extent of irradiation will be dependent on the thickness of the reaction mixture, concentration of photoinitiator and nature of substrate on to which the reaction mixture is coated and the source of UV.

These timings are for medium pressure mercury arc lamps as the source of UV operating at 100 W/cm. The intensity of UV @ 254 nm and 313 nm reaching the surface of the substrate is approximately 150 $\mu W/cm^2$ and 750 $\mu W/cm^2$. For a given lamp UV intensity in a function of the operating power and distance of the reaction mixture from the UV source.

In order to minimize and preferably eliminate the presence of any residual monomers it is important to ensure that the reaction is complete. This is dependent upon a number of factors such as the substrate onto which the adhesive is applied, the type and intensity of the ultra violet light and the number of ultra violet light passes. Preferably the conversion of the hydrophilic monomers present such as NaAMPS should be 98%, preferably 99.0% most preferably 99.9% so that the amount of monomer within the adhesive is 4600 microg/g or less, preferably 2300 microg/g or less, most preferably 230 microg/g or less.

The adhesive is provided, typically on at least a portion of the wearer facing surface of the flange, as a layer having a thickness or calliper C that is preferably constant, or that alternatively can vary over the surface of application of the adhesive.

When considering particularly the removal phase of an adhesive composition for attachment to the skin of a wearer, it is commonly recognised that good conditions of removal, i.e. at a frequency of about 100 rad/sec, of the adhesive applied to at least part of the wearer facing surface of the flange, are achieved when the adhesive can be easily removed from the skin, and particularly from the bodily hair that may be located on this area of the skin, where the flange contacts the body, without causing pain to the wearer, therefore without adhering too hard upon removal, to the skin and the hair of the wearer. Moreover, a good removal implies that the adhesive does not leave residues on the skin or on the hair.

The relationship between the thickness or calliper C measured in millimetres (mm) of the layer of the adhesive typically onto at least part of the wearer's facing surface of the flange of the disposable human waste management device, and the viscous modulus $G''_{25}$ at 25° C. at about 100 rad/sec of the topical adhesive gives an indication of painless and easy removal of the adhesive from the skin.

Without being bound to any theory, it is believed that for higher values of $G'_{25}$ at 100 rad/sec, which overall correspond to a higher adhesiveness of the composition, a thicker calliper or thickness C of the adhesive layer is needed so that the energy applied for the removal is more evenly distributed within the mass of the adhesive, and is therefore transferred smoothly to the skin, so avoiding peaks of energy that typically cause the pain sensation to the wearer. In other words, thinner layers of the adhesive necessitate an adhesive with a lower $G''_{25}$ at 100 rad/sec to achieve a reduced pain sensation upon removal of the device.

According to the present invention, the adhesive is preferably provided as a layer having a thickness C such that the viscous modulus $G''_{25}$ (100 rad/sec) and the thickness C of the adhesive layer satisfy the following empirical equation:

$$G''_{25} \leq [(7.00+C) \times 3000] \text{ Pa}$$

and preferably the following empirical equation:

$$G''_{25} \leq [(5.50+C) \times 1700] \text{ Pa}$$

While in a preferred embodiment of the present invention the thickness C of the adhesive layer is constant, such an adhesive layer can also have different thicknesses in different portions of the wearer facing surface of the flange where it is applied, provided that the above mentioned relationship between C and $G''_{25}$ is in any case satisfied in each portion.

In order to evaluate the effect of the thickness C of the adhesive layer in its relationship with the viscous modulus $G''_{25}$ (100 rad/sec) of the adhesive of the present invention on the removal of the adhesive used for the attachment of a disposable human waste management device to the skin of a wearer, a Removal Pain Grade Test has been developed. In this test the adhesion of standard substrates, on which the same adhesive has been provided in layers having different thicknesses, on the skin of the forearm of members of a sensory panel is achieved, and upon successive removal the pain is evaluated in terms of pain grade as described herein after.

According to the present invention any disposable human waste management device known in the art can be provided with the adhesive as defined herein.

Figure 4:
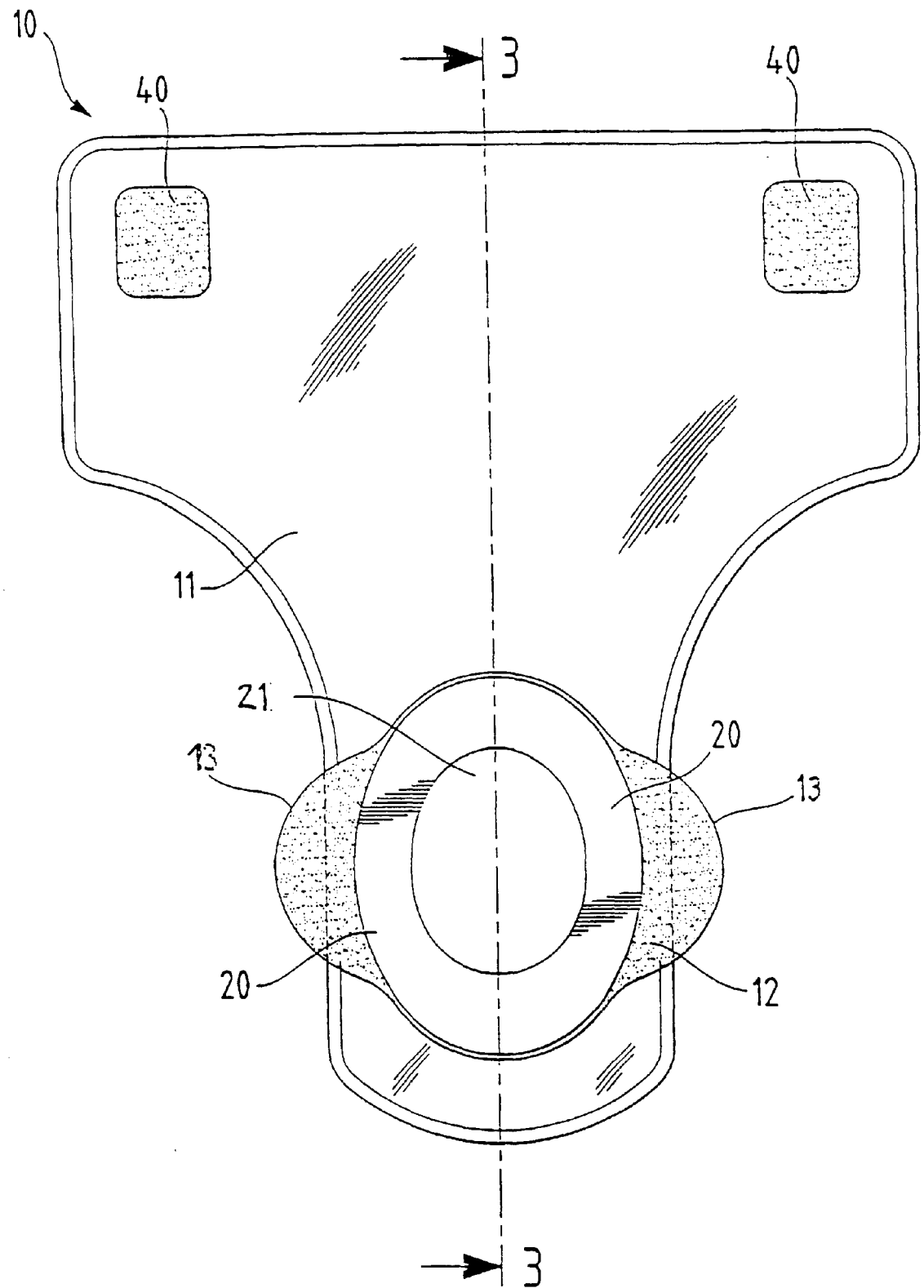
FIG. 4 is a plan view of a disposable urine management device of the present invention.

Typically urine or faecal management devices (10) comprise a bag (11) Shaving an aperture (21) and a flange (12) surrounding the aperture for preferably adhesive attachment to the uro-genital area and or the perianal area of a wearer as visible from FIGS. 1 and 4. According to the invention, any faecal or urine management device known in the art can be provided with an adhesive as defined therein.

The bag (11) as used herein is a flexible receptacle for the containment of urine and excreted faecal matter. The bag (11) can be provided in any shape or size depending on the intended use thereof, i.e. whether the device is intended for bedridden patients or active patients suffering from incontinence or requiring an artificial bowel or for infants. For example, elongated bags which are principally tubular or rectangular are typically utilised by bedridden patients and elderly incontinence sufferers. For more active wearers whether infants or adults, the disposal human waste management device should preferably be anatomically shaped such that the device follows the contours of the body and can be worn inconspicuously by the wearer under normal garments.

Particularly, preferred shapes are flat circular type bags, cone shaped bags, truncated shaped bags and pyramidal or truncated pyramidal shaped bags in a most preferred embodiment of a faecal management device of the present invention, the bag (11) has a substantially truncated cone shape. A preferred shape bag for urine devices is shown in FIG. 4. Typically the bags will have a wearer facing portion (16) and a garment facing portion (17). The wearer facing portion (16) of the faecal management device (10) is disposed adjacent the buttocks of the wearer. As such, the wearer facing portion (16) amply covers the buttocks of the wearer and does not hang between the thighs of the wearer.

In addition, the bag (11) is preferably shaped to allow at least partial insertion and retention of the bag between the buttocks of the wearer and thereby ensure good contact between the flange and the skin of the wearer. For example, the bag (11) may be provided with a neck portion or conduit.

The bag (11) is preferably designed to provide sufficient volume for urine and/or faecal material under a variety of wearing conditions, also when worn by a freely moving, i.e. not bedridden wearer. Sitting on the bag, for example, will result in a largely reduced volume in some areas of the bag. Thus, the bag (11) is preferably shaped to provide sufficient volume in areas which are not subjected to much pressure in wearing conditions such as sitting.

The bag (11) is designed to safely contain any entrapped material, typically it will be liquid impermeable, yet it may be breathable. The bag (11) is designed of sufficient strength to withstand rupture in use, also when pressure on the bag (11) is exerted in typical wearing conditions, such as sitting.

According to the present invention, depending on the shape of the bag (11) required, the bag (11) may be provided from a unitary piece of material or from a number of separate pieces of material, which may be identical or different and which are sealed at their respective peripheries.

In one preferred embodiment the bags herein have a wearer facing portion (16) and a garment facing portion (17) which comprise separate pieces of material. The wearer facing portion (16) and the garment facing portion (17) are sealed at the periphery of the bag (11), thus creating a bag peripheral rim (18). As is visible from FIG. 1, the wearer facing portion (16) of the bag (11) may comprise two further sections (19), which are secured to each other by means known to the man skilled in the art, such as adhesive, thermobonding or pressure bonding in order to provide the desired bag configuration. Said rim (18) may also be inside the bag, thus being coextensive with the inner surface (15) of the bag (11) rather than with the outer surface (30) of the bag (11). Preferably the bag (11) is asymmetrical to the transversal axis, so that the distance measured in the longitudinal direction from the centre of the aperture (21) to the front end of the bag (11) is shorter than the distance measured to the rear end of the bag (11).

According to the present invention the bag (11) can comprise one or multiple layers, preferably two or three layers. The layer on the inside of the bag (11), which will typically at least partially come in contact with faecal material is called the inner layer. The outermost layer of the bag, which will typically at least partially come in contact with the skin to the wearer and the garments of the wearer, is called the outer layer.

The layers of the bag material may be provided from any material, preferably so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose-wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., Ill, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (11) comprises three layers, preferably one film and two non-woven layers. In an even more preferable embodiment the film is interposed between the two non-woven layers. This sequence of layers results in a closed fibrous structure, which has a particularly pleasing sensation on contact with the skin of the wearer. In yet another preferred embodiment the inner layer comprises a film and the other two layers comprise non-wovens.

The non-woven layer or the non-woven layers comprised by the bag (11) may be hydrophobic or hydrophilic. If the bag (11) does not comprise a film layer, preferably at least one non-woven layer is hydrophobic. As a consequence, fluid penetration is resisted through the wearer facing portion (16) and the garment facing portion (17) of the faecal management device (10). If the bag comprises a film or a hydrophobic non-woven layer, further non-woven layers may be hydrophilic.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness of the wearer facing portion (16) and the garment facing portion (17). The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating on the wearer facing portion (16) and the garment facing portion (17) is transferable to the skin of the wearer by normal contact and wearer motion and/or body heat. Generally, mineral oil in the form of a lotion is recognised as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

In one embodiment of the present invention the bag (11) may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag or may be secured to the inner layer of the bag (11). Any known techniques for securing absorbent material to nonwoven and film substrates may be used to secure the absorbent material to the inner layer of the bag. The absorbent material may also be arranged to have any desired shape or configuration (e.g., rectangular, oval, circular, etc.).

In the embodiment shown in FIG. 4, the outer surface of bag (11) is provided with patches of adhesive (40) for securing the bag (11) to the body of the wearer. Preferably, the patches of adhesive (40) are positioned on the outer surface of bag (11) such that they are secured to the abdomen of the wearer in use. Any number, size and shape of adhesive patches (40) may be used depending on the intended use of the device.

The human waste management device in particular urine management devices according to the present invention also preferably comprise an additional acquisition layer. The acquisition layer is typically secured to the inner surface of bag. However, the acquisition layer may also be secured to the flange, or both the flange and the inner surface of bag. The acquisition layer is preferably positioned such that it separates the genitalia of the wearer from coming into direct contact with the absorbent material. The acquisition layer is fluid pervious allowing urine to readily pass through so that it may be absorbed by absorbent material.

The acquisition layer may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the acquisition, barrier layer includes fibers, the fibers may be spunbond, carded, wet-laid, meltblown, hydroentangled, or otherwise processed as is known in the art.

The acquisition layer is designed to have a pore size such that the absorbent material is not allowed to pass through and contact the wearer's skin. While designed not to have to large of a pore size which permits the passage of absorbent material, the acquisition layer preferably has a pore size which is greater than the pore size of the absorbent material.

Preferably, the acquisition layer is less hydrophilic than the absorbent material. The acquisition layer may be treated with a surfactant to increase its initial wettability. When treated with surfactant, however, the acquisition layer should still be less hydrophilic than the absorbent material. Suitable methods for treating the acquisition layer with a surfactant include spraying the acquisition layer with the surfactant and immersing the material into the surfactant. Alternatively, a surfactant may be incorporated into the acquisition layer.

As shown in FIG. 1 the bag (11) is provided with an aperture (21) whereby excreted matter is received from the body prior to storage within the bag cavity. The aperture (21) is surrounded by a flange (12) and may be provided in any shape or size, such as circular, oblong, heart shaped and may be symmetrical or asymmetrical, preferably the aperture has an oblong configuration either in the longitudinal or in the transversal direction or in both directions, e.g. the contours of the aperture are in the shape of two ellipses with the respective main axes being substantially perpendicular.

The flange (12) is attached to the bag (11) according to any means known to the man skilled in the art which may provide permanent or releasable attachment. Preferably however, the flange is attached to the bag by adhesive. Typically, the bag will be attached to the flange, towards the outer periphery of flange so as not to cause any obstruction for the entering matter.

The flange may be provided in any size depending on the wearer group for which the device is intended. Similarly the flange may be provided in any shape and preferably has a symmetrical shape preferably comprising a plurality of lobes (13, 14). The flange (12) may comprise a front projection (28) and a rear projection (29) to the perineal and coccygeal area of a wearer.

The flange comprises a garment facing surface (22) and a wearer facing surface (23). In an preferred embodiment these are two large, substantially flat surfaces, however, the flange may also comprise projections designed to fit the perineal or coccygeal area of the wearer.

The flange (12) should be made of soft, flexible and malleable material to allow easy placement of the flange to the perianal area. Typical materials include nonwoven materials, wovens, open -celled thermoplastic foams, closed-cell thermoplastic foams, composites of open-celled foams and stretch nonwoven, and films. A closed-cell foam of polyethylene has been found effective, but more preferably an open celled polyurethane foam is used. Preferably, such foams have a thickness within the general range of 0.1 to 5 millimetres and a density of 5 to 250 $g/m^2$, more preferably 50 $g/m^2$. Other thermoplastic foam materials, or other suitable plastics sheet materials having the described properties of such foams (i.e., softness, pliability, stretchability, and contractability) might also be used. Preferably, the material of garment facing surface (23) of the flange (12) may extend into the defined aperture area so as to form a skirt or flap of material which prevents unintentional adhesion of the surface edges of the flange defining the aperture to one another during use.

According to the present invention the adhesive (20) is preferably covered with a release means (not shown) in order to protect the adhesive (20), such as siliconized paper. The adhesive (20) can cover the entire wearer facing surface (23) of the flange (12) or more preferably have at least one, preferably two to six non-adhesive portions. These portions may be adhesive free or may contain inactivated or covered adhesives. As is evident from FIG. 1, the adhesive is in one preferred embodiment not applied to the entire wearer facing surface area of the flange (12), so as to provide lobes (13, 14) on either side of the flange (12) which are non-adhesive and can thereby serve to facilitate placement and removal of the device whilst avoiding contact with the adhesive. These lobes are however preferably also covered by the release means. Before application of the faecal management device (10) to the skin of the wearer, the release means if present is removed.

The adhesive (20) can be applied to the wearer facing surface of the flange (12) by any means known in the art such as slot coating, spiral, or bead application or printing. Typically the adhesive is applied at a basis weight of from 20 g/m² to 2500 g/m², more preferably from 500 g/m² to 2000 g/m² most preferably from 700 g/m² to 1500 g/m² depending on the end use envisioned. For example, for faecal management devices (10) to be used for babies the amount of adhesive may be less than for faecal management devices (10) designed for active adult incontinence sufferers.

Figure 2:
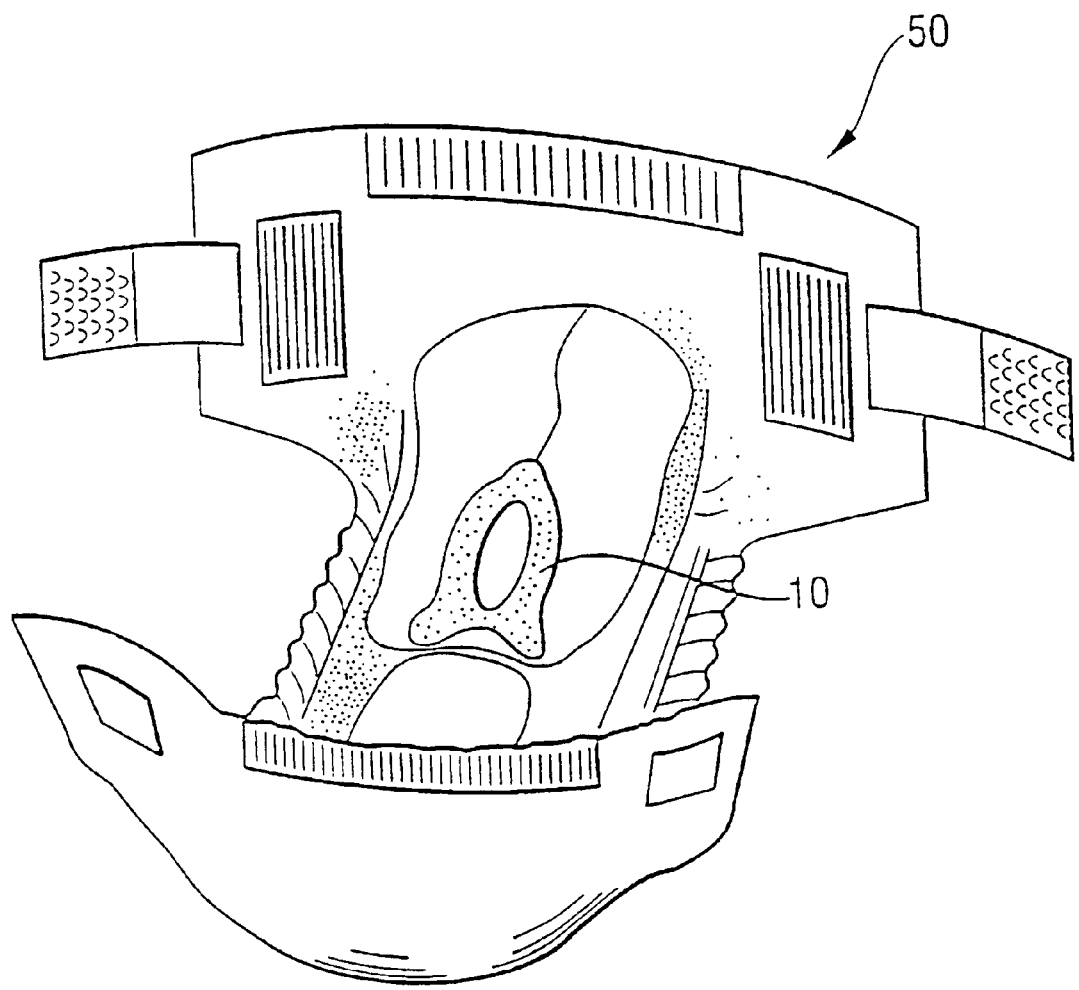
FIG. 2 shows a perspective view of the disposable faecal management device in conjunction with a disposable diaper.

The disposable human waste management device (10) of the present invention has been found to be particularly useful and beneficial when used in conjunction with a garment, or diaper (50), preferably a disposable diaper—refer to FIG. 2. The disposable human waste management device (10) is preferably first positioned in the perianal area of the wearer before the disposable diaper (50) is applied. In particular, the diaper (50) is positioned over the disposable human waste management device (10) and fastened in a conventional manner around the body of the wearer. It has been found that, in addition, to providing excellent separation between urine and faecal material, the combined disposable human waste management device (10) and diaper (50) system actually reduces skin irritation, which may at times occur, especially since the group of typical wearers includes the very old, the very young and the unhealthy wearers. In effect, the presence of the disposable human waste management device (10) permits the formation of a separation layer between the skin of the wearer and the diaper (50), i.e. a part of the absorbent core (58) of the diaper (10). The diaper (50) can be of the conventional type (an embodiment of which is described below although not a limiting example by any means) or can be adapted to contain in an effective and comfortable manner the disposal human waste management device (10) according to the teachings of the present invention.

As used herein, the term "disposable diapers" refers to articles which absorb and contain body extrudates; and more specifically, refers to articles which are placed against or in proximity to the body of the wearer to absorb and contain the various extrudates discharged from the body and which are intended to be discarded after a single use (i.e., they are not intended to be laundered or otherwise restored or reused) and, preferably, to be recycled, composted or otherwise disposed of in an environmentally compatible manner. As used herein, the term "diaper" refers to a garment generally worn by infants or incontinence sufferers that is drawn up between the legs and fastened about the waist of the wearer.

Figure 3:
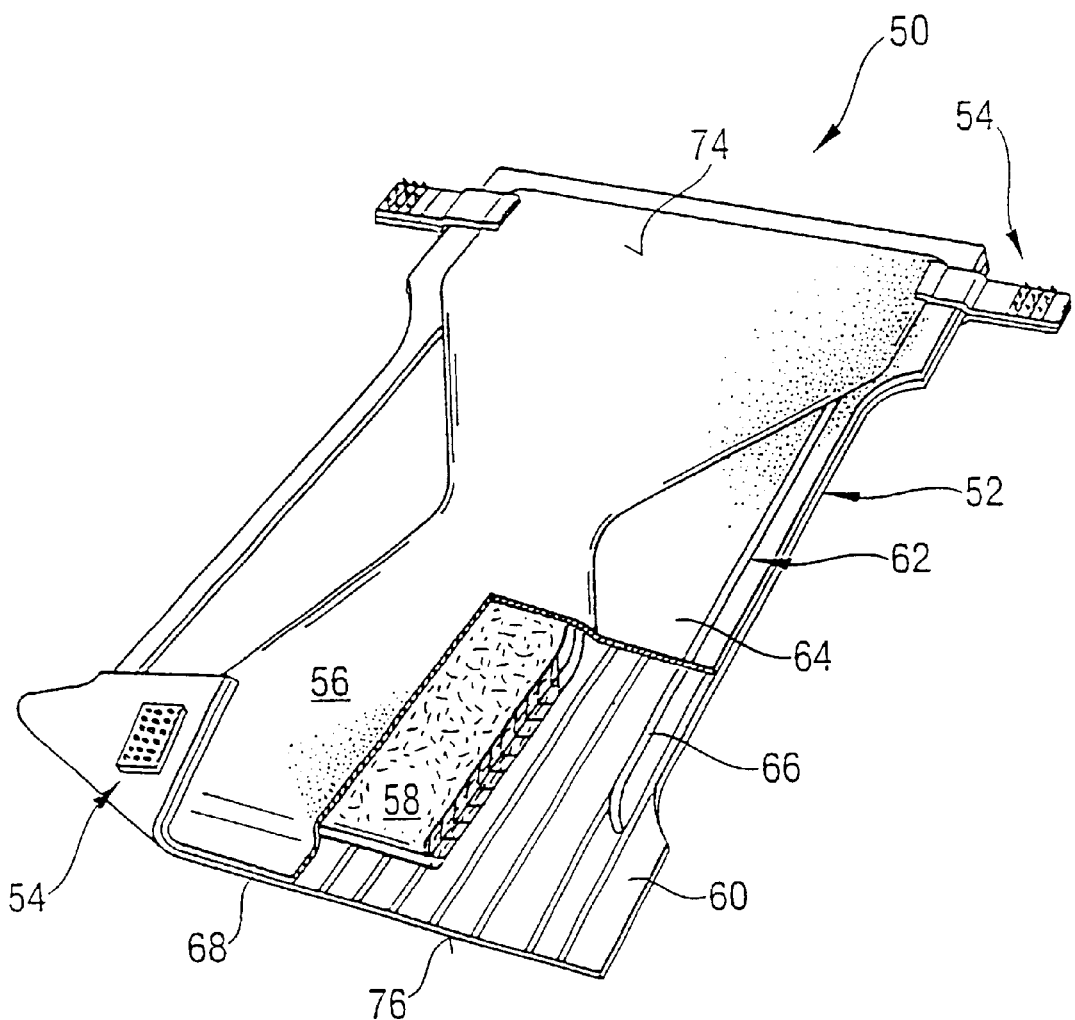
FIG. 3 is a partially cut-away perspective view of a disposable diaper embodying a faecal management device of the present invention.

FIG. 3 is a partially cut-away perspective view of a diaper (50) embodying the present invention prior to it being placed on the wearer over the faecal management device (10). As is visible from FIG. 3, a preferred diaper (50) comprises a body portion (52) and a refastenable mechanical fastening device (54). A preferred body portion (52) comprises a liquid pervious topsheet (56), and absorbent core (58), a liquid impervious backsheet (60), and elastically contractible leg cuffs (62); each leg cuff (62) preferably comprising a side flap,(64) and one or more elastic members (66). For simplicity purposes, only one elastic member (66) is shown in the side flap (64). While the topsheet (56), the absorbent core (58), the backsheet (60), the side flaps (64), and the elastic members (66) may be assembled in a variety of well-known configurations. A preferred disposable diaper configuration is shown and generally described in U.S. Pat. No. 3,860,003, an even more preferred disposable diaper configuration is shown and generally described in WO 93/16669. In this preferred diaper configuration, the backsheet (60) is joined to the topsheet (56); the absorbent core (58) is positioned between the topsheet (56) and the backsheet (60); the side flaps (64) extend outwardly from and along each side edge of the absorbent core (58); and the elastic member (66) is operatively associated with each side flap (64).

FIG. 3 shows the body portion (52) in which the topsheet (56) and the backsheet (60) are coextensive and have length and width dimensions generally larger than those of the absorbent core (58). The topsheet (56) is superposed on the backsheet (60) thereby forming the periphery (68) of the body portion (52).

The body portion (52) has an inside surface (74) and an outside surface (76). When a backsheet (60) is used, it typically forms the outside surface (76) of the body portion (52). The inside surface (74) is that surface of the diaper (50) opposite the outside surface (76) and in the embodiment shown is typically formed by the topsheet (56). In general, the inside surface (74) of the diaper (50) is that surface coextensive with the outside surface (76) and which is for the greater part in contact with the wearer when the diaper (50) is worn.

The absorbent core (58) of the body portion (52) may be any absorbent means which is generally compressible, conformable, non-irritating to the skin of the wearer, and capable of absorbing and retaining liquids such as urine and other certain bodily discharges. The absorbent core (58) may be manufactured in a variety of sizes and shapes (for example, rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core (58) may also be varied (for example, the absorbent core (58) may have varying calliper zones, hydrophilic gradients, superabsorbent gradients, or lower average density and lower average basis weight acquisition zones; or may comprise one or more layers or structures). Further, the size and absorbent capacity of the absorbent core (58) may be varied to accommodate wearers ranging from infants to adults.

The backsheet (60) is impervious to liquids (for example, urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (60) prevents the exudates absorbed and contained in the absorbent core (58) from soiling articles which are in contact with the diaper (50) such as undergarments and bedding. The backsheet (60) may thus comprise polymeric films such as thermoplastic films of polyethylene or polypropylene, or composite materials such as film-coated non-woven material. Exemplary films are manufactured by Tredegar Industries, Inc. of Terre Haute, Ind., USA or BP-Chemical PlasTec, Rotbuchenstrasse 1, D-8000 München, Germany.

The backsheet (60) is preferably textured to provide a more clothlike appearance. Further, the backsheet (60) may also permit vapours to escape from the absorbent core (58) while still preventing exudates from passing through the backsheet (60) by, for example, being supplied with microapertures. The size of the backsheet (60) is dictated by the size of the absorbent core (58) and the exact diaper design selected.

The topsheet (56) of the diaper is compliant, soft feeling and non-irritating to the skin of the wearer. Further, the topsheet (56) is liquid pervious permitting liquids (for example, urine) to readily penetrate through its thickness. A suitable topsheet (56) may be manufactured from a wide range of materials, such as porous foams, reticulated foams, apertured films; or woven or non-woven webs of natural fibres (for example, wood or cotton fibres) or from a combination of natural and synthetic fibres. Preferably, it is made of a material that isolates the skin of the wearer from liquids retained in the absorbent core (58).

There are a number of manufacturing techniques which may be used to manufacture the topsheet (56). For example, the topsheet (56) may be a non-woven web of fibres. An exemplary topsheet (56) is carded and thermally bonded by means well-known to those skilled in the fabric art. A suitable topsheet (56) is manufactured by, for example, Veratec Inc., a division of International Paper Company, of Walpole, Mass., USA. A topsheet (56) particularly preferred for incontinence garments comprises a formed thermoplastic film.

Test Methods

Removal Pain Grade Test

The Removal Pain Grade Test is utilized to evaluate the pain during removal from the skin of a wearer of a sample provided with a layer of a adhesive and previously attached to the wearer's skin. The test specifically evaluates the pain upon removal of each sample as compared to the pain obtained by removing a reference sample constituted by a commercial strong medical plaster.

Sample preparation.

The test is performed on rectangular samples 60×20 mm made of a polyester film 23 $\mu$m thick, such as that sold by Effegidi S.p.A. of Colorno (Parma, Italy), provided on one side with a continuous layer of the adhesive having the selected thickness. The reference sample is a 60×20 mm sample of an adhesive nonwoven fabric available from Beiersdorf A.G. Hamburg, Germany under the Tradename Fixomull™ stretch.

Test method.

A panel of six graders is selected for the test. The test is performed in a climatically controlled laboratory maintained at a temperature of 230° C. and a Relative Humidity of 50%. No special treatment of the wearer's skin is required beyond normal cleaning/washing with water and soap. The skin is then allowed to dry for at least two hours before the test to allow the skin to reach equilibrium with the room conditions. Different adhesive are evaluated in the test in comparison with the reference sample R. Each sample is applied by hand by an operator to the inner part of the grader's forearm, being centred between the wrist and the elbow, with the short side of the sample aligned with the length of the arm. The operator exerts on each sample with the palm of the hand the same pressure that is typically applied to cause a medical plaster to adhere to the skin. Each sample is worn for the prescribed time, and then it is removed from the grader's skin by the operator with a slow and smooth pull.

Four series of one reference sample R and the test samples are each applied, worn and then removed from the wearer's skin; each sample is worn for one minute, with a 5 minute wait between two subsequent samples of the same series, and a 15 minute wait between two different subsequent series. The reference sample R is always applied, worn and removed as the first sample of its respective series. The sequence of application/wear/removal of the test samples in each of the first three series is random, provided that no repetition in each series is allowed, and that no sequence is repeated in the first three series. In the fourth series one of the test samples is tested twice, the reference R always being the first one. Overall each sample has to be tested an equal number of times (24 times).

The graders were asked to evaluate each sample using a pain scale ranging from 0 to 10, where 0 corresponds to no pain and 10 corresponds to the pain upon removal of the reference sample R. The pain values for each sample were obtained as a mean of 24 observations.

The results collected from the test were analysed by a statistical analysis program "Comparison of Population Means—Paired Samples", that showed that the differences between the pain values of the samples are statistically significant.

Peel Adhesion Method

This is a quantitative method to determine the average peel force required to remove a skin at a specified peel angle and speed.

Equipment

| | |
|---|---|
| Scissors | Convenient source |
| Standard ruler | Convenient source |
| Steel Roller | 5.0 kg Mass. 13 cm in diameter and 4.5 cm in width covered with 0.5 mm thick rubber. |
| Polyester Film | PET 23$\mu$ available from EFFEGIDI S.p.A.,43052 Colorno, Italy. |
| Transfer Adhesive | 3M 1524 available from 3M Italia S.p.a. ,20090 Segrate Italy |
| Stop watch | Convenient source |
| Tensile Tester | Instron mod.: 6021( or equivalent) |

Test Procedure

A) Tensile Tester Peel Settings:

| | |
|---|---|
| Load cell | 10N |
| Test Speed | 1000 mm/min |
| Clamp to Clamp distance | 25 mm |
| Pre Loading | 0.2N |
| Test Path "LM" | 50 mm |
| Measure variable | F average (N) in "LM" |

B) Skin Condition and Preparation

The sample is peel from the forearm. There are 3 conditions of the skin that are tested:
1) Dry: The forearm is untreated and not wiped prior to test or between repetitions.
2) Wet: To one cotton disk (Demak'up diameter 5.5 cm, weight about 0.6 g), 3 ml of distilled water is added. Next the disk is then wiped with a light pressure 3 times over the test area on the forearm. (The test area of the forearm is a rectangle approximately 2 cm wider and longer than the adhesive area).

C) Sample Preparation
1. Allow the samples to adjust to conditioned room (23±2° Celsius and 50±2% RH) for about 1 hr.
2. Prepare rectangular adhesive samples 260 mm±2 length and 20 mm±2 wide.
3. Attach on the sample surface the polyester film (using the transfer adhesive to attach the polyester to the substrate surface).
4. Each test specimen should be prepared individually and tested immediately.
5. Remove the release paper from the adhesive without touching it. Attach one end to the skin (see section B).
6. Roll the Steel Roller for 160 mm along the adhesive strip, once in each direction.

D) Test Environment

There are 2 environments the adhesive can be tested in:
1) Conditioned Room as described in C1.
2) Wet Environment. Here, after step C4, the specimen is taken and put in a humidity controlled oven for 3 hours at 85 deg C. It is then taken out and steps C5, C6 are carried out.

E) Execution 1 minute after Step C6, take the free end of the specimen (approx. 100 mm long) and insert it in the upper end of the adhesion testing machine. Ensure the specimen is at a 90 degree angle to the forearm. Start the testing machine.

F) Report

Report the average of the peel strength of 5 tests. The single values are the base to calculate the standard deviation between the samples.

Residual Monomer Test Method

Test Sample 1 gram of a hydrogel sample is taken and emersed in 100 ml 0.9% saline water.

The sample is left in the saline at 40 deg C. for 24 hours.

An aliquot of the liquid is diluted and analysed by electrospray LC/MS/MS.

Calibration Sample 1 gram of reference monomers (eg NaAmps) are dissolved in 100 ml 0.9% saline water.

An aliquot of the liquid is diluted and analysed by electrospray LC/MS/MS.

Evaluation

The concentration of the test and calibration sample are determined by linear regression analysis using a software package such as VG Mass Lynx.

Adhesive Preparation

Suitable adhesives were prepared as described in the following Examples.

EXAMPLE 1

In 20 parts of polyethylene glycol diacrylate (pEG600) (product of UCB Chemicals marketed under the trade name designation of Ebacryl 11) were dissolved 6 parts of 1-hydroxycyclohexyl phenyl ketone (product of Ciba and marketed under the trade name designation of Irgacure 184). The solution so produced is herein designated solution A (XL/PI). Separately, 50 parts of the potassium salt of 3-sulphopropyl acrylate (SPA) (product of Raschig) were dissolved in 50 parts water to form solution B. A further solution designated solution C consisted of 50 parts water, 50 parts of the sodium salt of 2-acrylamido-2-methylpropane sulphonic acid (NaAMPS) product of the Lubrizol Corporation and marketed as a 50% aqueous solution under the trade name LZ2405). Mixtures of solutions B and C in the ratios of 100:0, 90:10. 60:40, 50:50, 40:60, 10:90 and 0:100 were made to form pre-gel solutions. To 80 parts of each of these pre-gel solutions, 0.15 parts of solution A, 5 parts potassium chloride and 20 parts distilled water were added. The pre-gel solutions were coated onto siliconised release paper at a coat weight of 0.8 kilograms per square meter and exposed to ultraviolet radiation by being passed under a medium pressure mercury arc lamp at a speed of 5 meters per minute to form clear self supporting gels. The residence time under the lamp was 4 seconds. The storage moduli(G') of 20 mm diameter discs stamped from the gels were recorded on a Rheometric Scientific RS-5 rheometer at 37° C. The G' values at 1 rad are recorded in Table 1. With the exception of the gels containing 90 and 100 parts SPA, the gels produced had acceptable tack and peel properties on the skin. From the data in Table 1 relatively linear changes in storage modulus are obtained on increasing or decreasing the SPA to NaAMPS ratio.

In the above Example, and in the following Examples wherever parts are mentioned they are meant as parts by weight unless otherwise specified.

TABLE 1

| NaAMPS Solution C | 80 | 72 | 48 | 40 | 32 | 8 | 0 |
|---|---|---|---|---|---|---|---|
| SPA Solution B | 0 | 8 | 32 | 40 | 48 | 72 | 80 |
| Distilled Water | 20 | 20 | 20 | 20 | 20 | 20 | 20 |
| XL/PI Solution A | 0.15 | 0.15 | 0.15 | 0.15 | 0.15 | 0.15 | 0.15 |
| KCl | 5 | 5 | 5 | 5 | 5 | 5 | 5 |
| G'(Pa) @ 1 rad/s | 4,198 | 3,389 | 2,471 | 2.205 | 1,759 | 703 | 492 |

EXAMPLE 2

In 20 parts of polyethylene glycol diacrylate (pEG600) (product of UCB Chemicals marketed under the trade name designation of Ebacryl 11) 6 parts of 1-hydroxycyclohexyl phenyl ketone (product of Ciba and marketed under the trade name designation of Irgacure 184) were dissolved. (This solution is designated solution A) (XL/PI). Separately 58 parts of the potassium salt of 3-sulphoproylacrylate (SPA) (product of Raschig) were dissolved in 58 parts distilled water to form solution D. A further solution designated solution E consisted of 42 parts water, 58 parts of the sodium salt of 2-acryiamido-2-methylpropane sulphonic acid (NaAMPS) (a product of the Lubrizol Corporation marketed as a 58% aqueous solution under the trade name LZ2405A). Mixtures of solutions D and E in the ratios 100:0, 90:10, 60:40, 50:50, 40:60, 10:90 and 0:100 were made to form pre-gel solutions. To 100 parts of each of these pre-gel solutions, 0.17 parts of solution A and 3 parts potassium chloride were added. The pre-gel solutions were coated onto siliconised release paper at a coat weight of 0.8 kilograms per square meter and passed under a medium pressure mercury arc lamp at a speed of 5 meters per minute to form clear self-supporting gels. Storage moduli were measured as in Example 1 and are recorded in Table 2. As 10 in the gels described in Example 1 the changes in the elastic or storage modulus G'(Pa) are linear with respect to the increasing or decreasing ratio of NaAMPS to SPA. All the gels produced possess acceptable tack and peel strength against skin. The gels with NaAMPS:SPA ratios in the range of 60:40 to 40:60, however, have a better balance of reusability and peel strength.

TABLE 2

| NaAMPS Solution E | 100 | 90 | 60 | 50 | 40 | 10 | 0 |
|---|---|---|---|---|---|---|---|
| SPA Solution D | 0 | 10 | 40 | 50 | 60 | 90 | 100 |
| XL/PI Solution A | 0.17 | 0.17 | 0.17 | 0.17 | 0.17 | 0.17 | 0.17 |
| KCl | 3 | 3 | 3 | 3 | 3 | 3 | 3 |
| G' (Pa) @ 1 rad/s | 15,142 | 14,333 | 11,073 | 10,672 | 9,920 | 6,280 | 5,199 |

Figure 5:
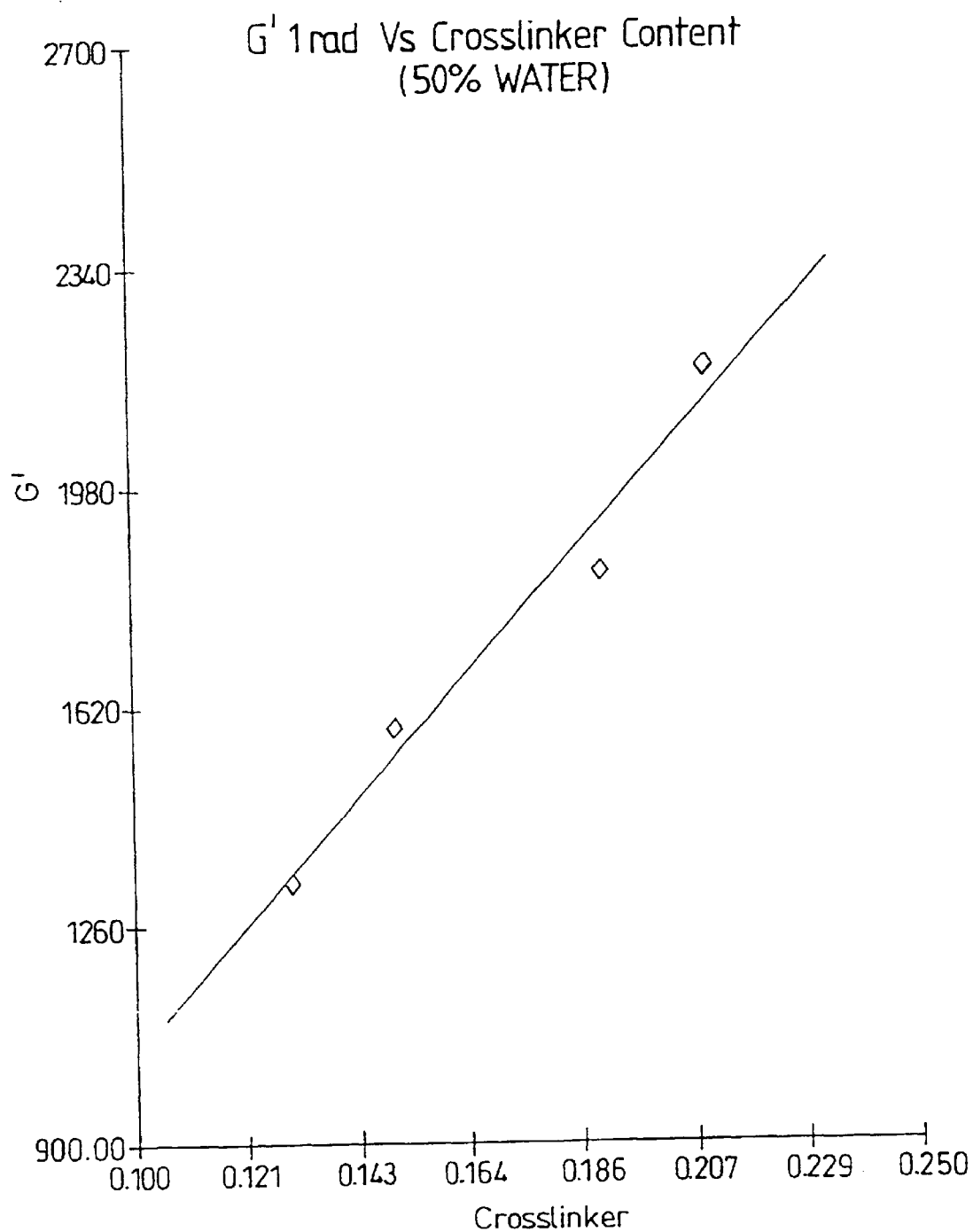
FIG. 5 is a graphical representation of the elastic modulus (G') versus crosslinker content.

Upon varying the amount of the cross-linking agent a substantially linear change in the elastic modulus G' can also be obtained, as illustrated by the graph of FIG. 5.

EXAMPLE 3

To 57 parts of a 58% solution of the sodium salt of 2-acrylamido-2-methylpropane sulphonic acid (NaAMPS) (LZ2405A) 10 parts of a 58% solution of the potassium salt of 3-sulphopropyl acrylate (SPA) were added along with 5 parts potassium chloride and stirred until the potassium chloride has dissolved. This solution was then mixed with 30 parts glycerol for 30 minutes. To the latter solution were added 0.15 parts of a solution containing 20 parts of polyethylene glycol diacrylate (pEG600) (product of UCB Chemicals marketed under the trade name designation of Ebacryl 11) in which 6 parts of 1-hydroxycyclohexyl phenyl ketone (product of Ciba and marketed under the trade name designation of Irgacure 184) were dissolved. The so-formed pre-gel solution was then cured as in Example 1. Good skin adhesion properties were obtained for this gel.

EXAMPLE 4

To 34.7 parts of a 58% aqueous solution of the sodium salt of 2-acrylamido-2-methylpropane sulphonic acid (NaAMPS) (LZ2405A) 34.7 parts of a 58% aqueous solution of the potassium salt of 3-sulphoproyl acrylate (SPA) were added along with 4.6 parts potassium chloride and 3 parts distilled water and stirred until the potassium chloride has dissolved. This solution was then mixed with 23.2 parts glycerol for 30 minutes. To the latter solution were added 0.15 parts of solution A prepared as described in Example 1. The so-formed pre-gel solution was then cured as in Example 1.

EXAMPLE 5

To 20 parts glycerol, 3 parts of a hydrophobic ethylene/ vinyl acetate copolymer emulsion (50% solids) (product of Harlow Chemicals marketed under the trade name DM137) and 10 parts polyethylene glycol (molecular weight 600) were added and stirred until a uniform colour was obtained. To this mixture were added 50 parts of a 58% solution of the sodium salt of 2-acrylamido-2-methylpropane sulphonic acid (NaAMPS) (LZ2405A), 16 parts potassium salt of 3-sulphopropyl acrylate (SPA) and 5 parts potassium chloride, and the solution was heated with stirring to 60° C. for one hour. The mixture had changed from an opaque off white to a translucent off white appearance. The turbidity of the solutions as measured in a portable turbidity meter, product code H193703 marketed by Hanna had changed from 254 ftu to 107 ftu. The solution was cooled to 20° C. and then there was added 0.13 parts of solution A prepared as described in Example 1. This final solution was stirred for one hour and then cured as in Example 1. The resulting gel had a G' value at 1 rad of 5328 Pa. The activity of water in the gel, as determined by placing the gel into cabinets at varying levels of humidity at 40° C. (40, 52, 64 and 80% RH) and measuring weight uptake or loss and extrapolating to zero weight change, was 0.62. The adhesion to skin of this gel was significantly greater than those described in the previous examples. Analysis of the gel by attenuated total reflectance infra-red spectroscopy revealed that in the surface regions (about 1 micron or less), either the air surface or the surface in contact with the release paper, the concentration of the ethylene/vinyl acetate copolymer relative to the NaAMPS was significantly enhanced compared to the bulk composition.

EXAMPLE 6

The method of Example 5 was carried out except that with the glycerol were added 3 parts of gum arabic. The resulting gel had a G' value at 1 rad of 5406 Pa. The activity of water as determined by the method in Example 5 was 0.55. The adhesion to skin of this gel was significantly greater than those described in the previous examples. Analysis of the gel by attenuated total reflectance infra-red spectroscopy revealed that in the surface region (about 1 micron or less), either the air surface or the surface in contact with the release paper, the concentration of the ethylene/vinyl acetate copolymer relative to the NaAMPS was significantly enhanced compared to the bulk composition.

EXAMPLE 7

The formulations shown in Table 3 were prepared using the following method which is for formulation 7a. To 33 parts glycerol, 10 parts of a hydrophobic ethylene/vinyl acetate copolymer emulsion (50% solids) (product of Harlow Chemicals marketed under the trade name DM137) were added and stirred until a uniform colour was obtained. To this mixture were added 35 parts of a 58% solution of the sodium salt of 2-acrylamido-2-methylpropane sulphonic acid (NaAMPS) (LZ2405A) and 15 parts potassium salt of 3-sulphopropyl acrylate (SPA), and the solution was heated with stirring to 60° C. for one hour. The solution was cooled to 20° C. and then there was added 0.15 parts of solution A prepared as described in Example 1. This final solution was stirred for one hour and then cured as in Example 1.

To prepare formulation 7b the same method used for formulation 7a was repeated except that the parts by weight were changed to the figures given in Table 3.

To prepare formulation 7c the same method used for formulation 7a was repeated except that a propylene oxide/ethylene oxide block copolymer surfactant (designated PE/F127 and manufactured by BASF) was added with the glycerol and the parts by weight were changed to the figures given in Table 3.

TABLE 3

| | COMPOSITION by WEIGHT | | |
|---|---|---|---|
| Formulation | 7a | 7b | 7c |
| 58% NaAMPS | 35 | 35 | 35 |
| SPA | 15 | 25 | 25 |
| Glycerol | 33 | 20 | 20 |
| DM 137 | 10 | 15 | 15 |
| PEG 600 | 5 | 10 | 10 |
| PE/F127 | | | 1 |
| PI/XL (Solution) | 0.15 (A) | 0.14 (A) | 0.14 (A) |

As will be seen, the invention presents a number of different aspects and it should be understood that it embraces within its scope all novel and inventive features and aspects herein disclosed, either explicitly or implicitly and either singly or in combination with one another. Also, many detail modifications are possible and, in particular, the scope of the invention is not to be construed as being limited by the illustrative example(s) or by the terms and expressions used herein merely in a descriptive or explanatory sense.

What is claimed is:

1. A disposable human waste management device (10) comprising a bag 11, said bag (11) having an aperture and a flange (12) surrounding said aperture (21), said flange (12) having a wearer facing surface (23) and a garment facing surface (22), wherein said wearer facing surface comprises an adhesive (20), wherein said adhesive has:
   (1) a water activity of from 0.4 to 0.9;
   (2) an elastic modulus at 1 rad/s (37° C.) of from 700 to 15,000 Pa;
   (3) an elastic modulus at 100 rad/s (37° C.) of from 2000 to 40,000 Pa;
   (4) a viscous modulus at 1 rad/s (37° C.) of from 450 to 14,000 Pa;
   (5) a viscous modulus at 100 rad/s (37° C.) of from 1000 to 35,000 Pa; and
   wherein the viscous modulus is less than the elastic modulus in the frequency range of from 1 to 100 rad/s.

2. The disposable human waste management device according to claim 1, wherein the adhesive comprises a hydrophobic polymer and wherein the concentration of the polymer at the surface of the adhesive is greater than the concentration in the remainder of the adhesive.

3. The disposable human waste management device according to claim 1, wherein the adhesive comprises an aqueous plasticiser, a copolymer of a hydrophilic unsaturated water-soluble first monomer and a hydrophilic unsaturated water-soluble second monomer, and a cross-linking agent.

4. The disposable human waste management device according to claim 1, wherein the adhesive is prepared by polymerising an aqueous reactive mixture comprising a hydrophilic unsaturated water-soluble first monomer, a hydrophilic unsaturated water-soluble second monomer, and a cross-linking agent.

5. The disposable human waste management device according to claim 4, wherein the first monomer is capable of enhancing the mechanical strength of the composition and/or the second monomer is capable of increasing the water activity of the composition.

6. The disposable human waste management device according to claim 5, wherein the first monomer is a compound of the formula:

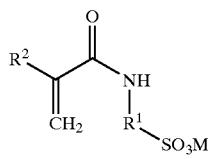

(I)

wherein $R^1$ is a substituted hydrocarbon moiety, $R^2$ is hydrogen or substituted methyl and/or substituted ethyl, and M represents hydrogen or a cation.

7. The disposable human waste management device according to claim 6, wherein the second monomer is a compound of the formula:

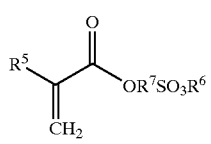

(II)

wherein $R^5$ represents hydrogen or a substituted methyl and/or substituted ethyl, $R^6$ represents hydrogen or a cation, and $R^7$ represents a substituted alkylene moiety of 1 to 4 carbon atoms.

8. The disposable human waste management device according to claim 7, wherein the first monomer is 2-acrylamido-2-methylpropanesulphonic acid or an analogue thereof or one of its salts, and/or the second monomer is a polymerisable sulphonate or a salt of acrylic acid (3-sulphopropyl)ester or an analogue thereof.

9. The disposable human waste management device according to claim 8, wherein the ratio of the first monomer to the second monomer by weight is from 20:1 to 2:3.

10. The disposable human waste management device according to claim 9, wherein the aqueous reactive mixture further comprises a compound selected from the group consisting of a surfactant, an additional monomer, an electrolyte, a water soluble polymer suitable for forming an interpenetrating polymer network, a lipid-micellising polymer, a non-hydrophilic polymer, and/or an antimicrobial agent.

11. The disposable human waste management device according to claim 1, wherein said disposable human waste management device (10) is disposable proximate to a disposable diaper (50).

12. A disposable article comprising:

(a) a diaper (50); and, (b) a disposable human waste management device (10); wherein said disposable human waste management device further comprises a bag (11), said bag (11) having an aperture and a flange (12) surrounding said aperture (21), said flange (12) having a wearer facing surface (23) and a garment facing surface (22), wherein said wearer facing surface comprises an adhesive (20), wherein said adhesive has:

(1) a water activity of from 0.4 to 0.9;

(2) an elastic modulus at 1 rad/s (37° C.) of from 700 to 15,000 Pa;

(3) an elastic modulus at 100 rad/s (37° C.) of from 2000 to 40,000 Pa;

(4) a viscous modulus at 1 rad/s (37° C.) of from 450 to 14,000 Pa;

(5) a viscous modulus at 100 rad/s (37° C.) of from 1000 to 35,000 Pa; and wherein the viscous modulus is less than the elastic modulus in the frequency range of from 1 to 100 rad/s.

* * * * *